United States Patent
Anderson et al.

(10) Patent No.: US 8,196,455 B2
(45) Date of Patent: Jun. 12, 2012

(54) SENSOR

(75) Inventors: Henrik Anderson, Järfälla (SE); Henrik Björkman, Uppsala (SE); Teodor Aastrup, Djursholm (SE)

(73) Assignee: Attana AB, Stockholm (SE)

( * ) Notice: Subject to any disclaimer, the term of this patent is extended or adjusted under 35 U.S.C. 154(b) by 441 days.

(21) Appl. No.: 12/598,424

(22) PCT Filed: Apr. 30, 2008

(86) PCT No.: PCT/GB2008/001515
§ 371 (c)(1),
(2), (4) Date: Oct. 30, 2009

(87) PCT Pub. No.: WO2008/132487
PCT Pub. Date: Nov. 6, 2008

(65) Prior Publication Data
US 2010/0116035 A1    May 13, 2010

(30) Foreign Application Priority Data

Apr. 30, 2007  (GB) .................................. 0708346.2

(51) Int. Cl.
*G01N 29/00* (2006.01)
(52) U.S. Cl. ...................................................... 73/61.49
(58) Field of Classification Search .................. 73/61.49
See application file for complete search history.

(56) References Cited

U.S. PATENT DOCUMENTS

| | | | |
|---|---|---|---|
| 5,955,771 A * | 9/1999 | Kurtz et al. | 257/419 |
| 6,210,989 B1 * | 4/2001 | Kurtz et al. | 438/51 |
| 6,418,926 B1 * | 7/2002 | Chawla | 128/203.12 |
| 7,013,834 B2 * | 3/2006 | Tyler et al. | 118/723 E |
| 2006/0199260 A1 * | 9/2006 | Zhang et al. | 435/293.1 |
| 2007/0042377 A1 * | 2/2007 | Gao et al. | 435/6 |
| 2009/0310743 A1 * | 12/2009 | Carpenter et al. | 378/45 |

\* cited by examiner

*Primary Examiner* — Hezron E Williams
*Assistant Examiner* — Rodney T Frank
(74) *Attorney, Agent, or Firm* — Banner & Witcoff, Ltd

(57) ABSTRACT

A sensor element carrier for use in a mass-sensitive chemical sensor instrument comprises a base component and a lid component, the base component being adapted to receive, in use, a sensor, the signal generated by which depends on the mass of material adsorbed at a sensing surface thereof, the base component or the lid component having formed therein, in a recessed area, at least one channel for the ingress of sample fluid, the recessed area forming, in use and in conjunction with the sensing surface of the sensor, a sample chamber, the sensor being held, in use, between the base component and the lid component and the approach of the base component and lid component being limited on assembly of the sensor element by means of substantially rigid portions of each which come into abutment, thereby limiting the minimum height of the sample chamber for a given set of sensor, base and lid components.

28 Claims, 9 Drawing Sheets

SENSOR

This invention relates to mass-sensitive chemical sensors. In particular, though not exclusively, it relates to sensor elements and related ancillary apparatus for use in mass-sensitive chemical sensor instruments.

A mass-sensitive chemical sensor can be defined as any device that allows for measurement of a property that scales proportionally to mass associated with or bound to a sensing surface of that device. Several such sensor techniques can be utilised, such as evanescent wave-based sensors, e.g. surface plasmon resonance (SPR, which is capable of registering mass changes by the associated change in refractive index at the surface), optical waveguides (also dependent on refractive index changes associated with mass binding events), optical diffraction, optical interference, ellipsometry and acoustic wave devices (for example quartz crystal micro balances (QCMs)). These sensor approaches are well established in the art (see, for example, *Biomolecular Sensors*, Gizeli and Lowe. Taylor and Francis, London; 2002) and these types of instruments can be used for studies of chemical reactions in situ and for detection of certain molecules in a sample.

A QCM system utilizes the piezoelectric effect of a quartz crystal. In such a system a quartz crystal that is placed between two electrodes, which are connected to an AC-potential, begins to oscillate if the frequency of the AC-potential is close to the resonance frequency of the oscillation mode for the quartz crystal. The resonance frequency of the quartz crystal is a function of many parameters, such as temperature, pressure, cut angle of the crystal, mechanical stress and thickness of the crystal. The resonance frequency is inversely proportional to the thickness of the crystal.

Typical resonance frequencies used in liquid applications range from 1 MHz to 50 MHz. The crystal is normally AT-cut with a circular or square shape with a diameter of approximately 5-10 mm. The electrodes (driving and counter electrodes) are normally of gold on both sides, but other metals are not unusual. The electrodes are very thin compared to the quartz crystal plate and can therefore be considered as part of the crystal plate. When material is added to or removed from one of the electrodes, it becomes thicker or thinner, i.e. the associated weight of the electrode changes. As a consequence of the mass change of the electrode, the resonance frequency of the crystal plate will either decrease or increase and hence the change of resonance frequency can be measured to detect the mass change of the electrode. The mass resolution of a QCM system can be as low as 1 pg/cm$^2$, corresponding to less than 1% of a monolayer of hydrogen.

A typical QCM piezoelectric sensor instrument comprises a sensor element, a sample insertion unit, equipment for determining the piezoelectric properties (including the oscillation frequencies) of a quartz crystal, and signal presentation equipment and buffer and waste containers (other than the sensor element, these items may be referred to as the 'associated apparatus' of the sensor instrument). A sample, which can contain any chemical substance of interest, is introduced into the sensor element by the sample insertion unit. The sensor element contains a piezoelectric resonator (the QCM sensor), a sample chamber, flow channels to and from the chamber and an oscillating circuit. The sample induces an interaction with the piezoelectric sensor surface, which can in turn be observed by monitoring the oscillating characteristics of the crystal plate, e.g. by measuring changes in the piezoelectric resonator frequency. The crystal plate is provided with electrical contact areas for the driving and counter electrodes on its surface, such contact areas being connectable to a signal source (e.g. an alternating voltage source) as well as to a measurement device. For measuring, the piezoelectric crystal plate is on one side brought into contact with the fluid (e.g. liquid) sample to be examined. The crystal responds to the accumulation of the mass of the substance to be detected or to a change in the physical properties of the sample by altering its resonance frequency and/or oscillation amplitude.

Piezoelectric sensors can be used for analysis of the viscosity of a liquid sample and are particularly suitable for studying chemical and biochemical interactions. If a piezoelectric sensor is to be used for the latter purpose, the electrode that is to be exposed to the sample is provided with a specific surface coating, which will interact with the sample.

Such surface coated piezoelectric sensors can be used within, for example, surface science, biotechnology research and pharmaceutical research. Other applications can be as a sensor for detection of hazardous gases or substances such as environmental contaminants, biochemical warfare agents and illicit drugs, e.g. narcotic substances or performance improving drugs. A third area for application of the technology is health diagnostics, where the sensor can be used for examining patients for different diseases by analysis of human blood or other body fluids.

As already mentioned piezoelectric resonators are advantageously used as active sensors, e.g. for detecting and/or measuring a substance in a medium. When working with liquids, the oscillator quartz to be electrically contacted has also to be insulated liquid-tight against the liquid to be examined in order to prevent electrical short circuits. Such a sensor is described in EP 453820. This sensor element provides a small oscillator quartz plate, which is clamped on both sides between two silicone seals and, in addition, is contacted to conductive adhesive substances. However, the use of conductive adhesives has the consequence that the electrical contact cannot be disconnected, which, for instance, makes replacing the small oscillator quartz plate difficult, requiring great manual skill. Moreover, the silicone seals surrounding the small oscillator plates on all sides have to be made with great precision in order to prevent deformations in the small plate.

In WO 2004/057319, a QCM sensor element and associated apparatus of a sensor instrument are described. The sensor element comprises a carrier into which a QCM sensor mounted on electrodes is fitted. The sensing surface of the QCM sensor (i.e. the electrode which will become exposed to sample fluid) is fully exposed to the external environment once the carrier and sensor are assembled. The sensing surface is only sealed from the external environment once the sensor element is engaged with a substantially cylindrical compressible element of the associated apparatus, the substantially cylindrical element having a recess formed therein which, in conjunction with the sensing surface of the QCM sensor, forms a flow cell (or flow-through cell) for sample fluids. The height of the flow cell in such an arrangement is therefore dictated by the degree of compression applied to the substantially cylindrical element. Uniformity of flow cell/sample chamber height is of importance to achieving reproducible results between samples. One of the additional disadvantages of this arrangement is that it is not possible to store the sensor element 'wet' away from the associated apparatus of the sensor system.

U.S. Pat. No. 6,196,059 discloses a carrier for a QCM sensor, the carrier consisting of a support member having an indentation therein for receiving the sensor. The sensor is held on a platform, at the circumference of which is a raised rib. The sample chamber is formed by the surfaces of the platform, the sensor and the rib. The sensor is fixed to the rib by means of a layer of adhesive substance. The sample chamber height is therefore variable depending on the thickness of adhesive applied, and the amount of pressure applied to the sensor to cause it to adhere and seal the sample chamber. Both these variables are ultimately dependent on the user and thus very difficult to control, thereby resulting in a loss of reproducibility. An additional problem with reliance on adhesives is that they present a risk of contamination of the sensing surface and/or the test sample with components of the adhesive composition.

In WO 02/12873, a flow cell for a QCM sensor is described. The QCM sensor is mounted, using adhesive and gravity (the application of additional pressure is avoided so as to reduce stresses in the crystal), on the underside of a flange protruding into a cylindrical void in a lower part of the flow cell. The upper part of the flow cell is engaged with the upper side of the flange via an O-ring seated thereon. The height of the sample chamber/flow cell is thus partially dependent on the degree of compression applied to the O-ring. If the flow cell is assembled such that the upper part engages with the upper side of the flange, sample height chamber is better controlled, but the variable mounting of the sensor, which will be dependent on the thickness of the adhesive, the weight of the sensor and the adhesion time, will still inevitably lead to variations in sample chamber height both in a given flow cell and between flow cells. As mentioned above, the use of adhesives also presents the problem that the sensor cannot be removed from the sensor element after use, and that components of the adhesive composition can contaminate the sensing surface and/or test sample.

It is therefore an object of the present invention to provide sensor elements, and carriers for the construction thereof, which variously address the problems identified above in connection with the prior art.

Accordingly, one aspect of the present invention provides a sensor element carrier for use in a mass-sensitive chemical sensor instrument, the sensor element carrier comprising a base component and a lid component, the base component being adapted to receive, in use, a sensor, the signal generated by which depends on the mass of material adsorbed at a sensing surface thereof, the base component or the lid component having formed therein, in a recessed area, at least one channel for the ingress of sample fluid, the recessed area forming, in use and in conjunction with the sensing surface of the sensor, a sample chamber, the sensor being held, in use, between the base component and the lid component and the approach of the base component and lid component being limited on assembly of the sensor element by means of substantially rigid portions of each which come into abutment, thereby limiting the minimum height of the sample chamber for a given set of sensor, base and lid components.

The sensor element carrier of the present invention has the advantage that the height of the sample chamber is uniform and predictable for a given set of base and lid components and sensor. When the base and lid components are brought together during assembly of the sensor element, the recess formed in one of these components and which forms the 'ceiling' of the sample chamber in use is unable to approach the sensor beyond the point at which the substantially rigid portions of the base and lid components abut. In other words, for a given combination of sensor and base and lid components, normal assembly of the sensor element should result in the same sample chamber height every time. Unlike in many prior art sensor elements, the sensor does not have to be mounted in the sensor element carrier of the present invention by means of a layer of adhesive whose thickness is ultimately variable.

The sensor element carrier of the present invention also allows a very precise control of sample chamber height to be manufactured into the sensor element. It allows the production of very low height sample chambers (by means of correspondingly shallow recessing of the recessed area). Such chambers provide higher flow velocities (for a given flow rate) and reduce the influence of diffusion effects on molecular interactions (by reducing the thickness of the stagnant layer adjacent the sensor surface, through which layer the analyte has to diffuse to reach the sensor surface). These factors improve the accuracy of kinetic analyses and allow the measurement of more complex biological reactions to be achieved.

As used herein, the term 'substantially rigid' implies that the portion of the carrier concerned does not deform under normal assembly and use of the carrier to such an extent as to affect reproducibility of the sample chamber height. It is preferred that the base and lid components of the carrier are both constructed in their entirety from substantially rigid material or materials. The attachment of the base and lid components to each other during assembly of the sensor element for use thereof may be achieved by known means, e.g. by means of screws passing through apertures in the components, or via resilient clamps. The only requirement is that the attachment means bring the substantially rigid portions of the components into abutment. It will be appreciated that a given base component can be combined with a variety of lid components (or vice versa) to allow different sample chamber heights to be achieved. The different lid components or base components (whichever has the recessed area) are simply required to have different depths of recessing of the recessed area.

In a preferred embodiment, the sensor element carrier further comprises a compressible sealing member surrounding the recessed area, the compressible sealing member protruding beyond the recessed area and beyond the non-recessed portion of the base or lid component surrounding the recessed area, such that the compressible sealing member abuts, in use, the surface of the sensor so as to form the lateral edges of the sample chamber.

The compressible sealing member helps to achieve a better seal of the sample chamber, thereby avoiding leakage of sample fluids and isolation of the sample chamber from the external environment. During assembly of the sensor element, the compressible sealing member, due to its protrusion beyond the recessed area and the surrounding non-recessed area of the base or lid component, should come into contact with the surface of the sensor before the substantially rigid portions of the base and lid components abut. As the base and lid components are brought even closer together, the compressible sealing member is compressed, so as to provide the improved sealing of the sample chamber, until the point at which the substantially rigid portions abut. No further compression of the sealing member is possible and the predictable sample chamber height is preserved. In preferred embodiments, the compressible sealing member is seated within a groove formed in the base or lid component between the recessed area and the surrounding non-recessed area.

As an alternative to the use of a compressible sealing member, the sensor may be attached, in use, to the base or lid component having the recess formed therein, so as to cover the recess, by means of an adhesive applied between the sensor and base or lid component in the region surrounding and adjacent the recess. The adhesive layer seals the sensor across the recess, so as to form the sample chamber. When the sensor element is assembled, however, the base and lid components of such an embodiment urge the sensor against the adhesive layer such that the sample chamber height is reduced until the substantially rigid portions of the base and lid components abut. In such a way, sample chamber height is still controlled by the abutment of the base and lid components. Certain prior art problems associated with the use of adhesives in sensor elements are thereby avoided. A suitable adhesive substance may be, for example, a curable silicone adhesive which results in a resilient layer of adhesive.

The compressible sealing member is preferably an elastomeric ring having a cross-sectional shape which is capable of deformation, upon application of axial force, by bending. A number of such cross-sectional shapes may be envisaged. The common feature of rings having such cross sections is that, not only do they deform by compression and redistribution of their elastomeric material, they also deform by bending about one or more points within the cross-sectional shape. It will be appreciated that an O-ring, on the other hand, is only capable of deformation by compression and redistribution of elastomeric material (i.e. so as to form an ellipsoidal cross-section, at least initially, in the absence of radial restriction). Bendable cross-sectional-shaped rings are generally more compressible for a given applied force and hence can be formed from harder, more chemically inert materials. It will be understood that the term 'ring' as used in connection with such compressible sealing members, does not imply a restriction to such members having a circular shape. Other shapes of compressible sealing member are intended to be covered by the present invention, although circular members may be preferred.

In preferred embodiments, an 'X'-shaped, or equivalent, cross section is used.

A compressible sealing member of this type, also known as an X-ring, allows sealing pressure to be applied to the surface of the sensor over a relatively small area, thus avoiding excessive damping of a QCM-based sensor, or mechanical damage to sensors in general. With QCM-based sensors, limitation of applied pressure is especially important when higher frequency crystals (e.g. 20 MHz or above) are used. The higher resonant frequency of such crystals dictates a reduced crystal thickness and hence a correspondingly more fragile quartz substrate. The use of an X-ring, or equivalent, allows such high frequency crystals to be more readily employed. An equivalent cross section to 'X'-shaped is any shape which allows sealing pressure to be exerted via two or more separate arms of the cross section. Thus, equivalent cross sections include 'Y'-shaped, 'U'-shaped, 'V'-shaped, 'A'-shaped or 'H'-shaped, and all such equivalents are intended to be included within references to X-rings and related terms herein. Elastomeric rings of 'X'-shaped cross section are preferred owing to the relatively symmetrical nature of the cross section (which makes them more predictable to work with) and their greater availability. X-rings, or equivalents, owing to the conformational flexibility (i.e. bending) of their cross-sections, and the low area of the sensor over which they exert sealing pressure, can be formed from harder materials than, for example, 'O'-rings and yet still be compressible enough to provide adequate sealing without damaging the sensor. Harder materials (such as, for example, fluoropolymers or nitrile rubber) have the advantage of being more chemically resistant.

In a typical embodiment, the X-ring, or equivalent, is seated in a groove formed in the base or lid component surrounding the recessed area, the groove being deeper than the recess. Typically, two arms of the cross section of the X-ring, or equivalent, protrude from the groove. Alternatively, in the case of a compressible sealing member having a 'Y'-shaped cross-section, the sealing member may be inverted such that a single arm protrudes from the groove. This arrangement allows the sealing member still to provide the appropriate conformational flexibility, sealing pressure and low area of pressure exertion/force transmission on the sensor. A similar effect can be achieved with a compressible sealing member having a kinked 'I'-shaped cross-section. The kink leads to a cross-sectional shape approximating to '>' (i.e., similar to the left hand portion of an 'X').

An alternative to an X-ring, although less preferred, is a ring having a substantially square cross-section, or, less preferably, an O-ring having a suitably low diameter cross section. Both these types of sealing member exert greater force on the sensor than the X-ring. The O-ring should preferably have a lower diameter cross section than the width of cross section of the X-ring to ensure that sealing pressure may be applied with minimal contact of, and force exerted on, the sensor.

When an X-ring is used in the carrier of the present invention, it is preferred that, in use, the elastomeric ring and the sensor are arranged such that only the inner protruding leg of the 'X'-shaped cross section contacts the sensor and is less compressed than the outer protruding leg which contacts the base component or lid component.

Such an arrangement can be achieved, for example when the compressible sealing member and recessed area are in the lid component, by having the base component adapted to receive the sensor such that the sensor sits lower than the surrounding and adjacent surface of the base component, the outer edge of the sensor being, once placed into the base component, in approximate registration with the centre of the X-shaped cross section of the X-ring. The inner (i.e. towards the centre of the X-ring) protruding leg of the X-ring will thus contact the sensor (whose surface is lowered), whilst the outer (i.e. away from the centre of the X-ring) protruding leg of the X-ring will contact the surrounding and adjacent surface of the base component (whose surface is raised relative to the sensor surface). The outer protruding leg will thus, on assembly of the sensor element, be more compressed than the inner protruding leg. The advantage of this difference in compression is that the pressure applied to the sensor can be reduced to a level which avoids excessive damping and/or mechanical damage to the sensor, whilst still ensuring a higher pressure seal of the sensor element overall as a result of the compression of the outer leg of the X-ring against the carrier. The outer, higher pressure seal helps to prevent fluids from entering the carrier from the external environment. Such fluids could otherwise potentially gain access to the sensor, thereby affecting the characteristics thereof. The assembled sensor element is thus more robust under different environmental conditions (e.g. humidity variations, or condensation following removal of the sensor element from refrigeration into an ambient environment) and suitable for instance for storage of a used or activated sensor.

In certain embodiments, a larger diameter QCM crystal may be used (e.g. around 10 mm diameter, or a square QCM crystal of around 10 mm×10 mm). In such embodiments in particular (although in other embodiments employing smaller QCM crystals also), the X-ring may not necessarily extend radially beyond the edge of the crystal as described above, but may instead seal the crystal at a region inward from the edge thereof. It will be appreciated that such an arrangement does not affect the sealing and sample chamber height control achieved by sensor element carriers of the present invention.

In embodiments of the sensor element carrier having a compressible sealing member, it will be understood that the recessed area of the base or lid component need only be 'recessed' relative to the extent of protrusion of the sealing member. Whilst, in most embodiments, the recessed area will also be recessed relative to the 'non-recessed' surrounding area of the base or lid component, in certain embodiments it is possible for the recessed area, i.e. which forms the ceiling of the sample chamber in use, to actually be level with or protrude beyond the surrounding area of the base or lid component, provided that the compressible sealing member protrudes yet further. For instance, in an embodiment in which the recessed area is formed In the lid component, the recessed area may protrude beyond the surrounding area of the lid component; such a lid component may be assembled with a base component having a correspondingly deepened area for receiving a sensor. On assembly, the protruding sealing member and recessed area extend into the correspondingly deepened area of the base component to seal the sensor element. The use of a deeper area for receiving the sensor makes assembly of the sensor element more simple and reproducible. Preferred compressible sealing members for use with such embodiments include the kinked 'I'-shaped and 'Y'-shaped cross-section rings described above.

Preferably, the recessed area having the at least one channel is formed in the lid component.

In preferred embodiments, the recessed area has a first channel formed therein for the ingress of sample fluid, and a second channel formed therein for the egress of sample fluid, such that the sample chamber can be used as a flow cell.

The advantages of flow cells are known in the art. They provide ready access to the sensor surface for multiple samples and facilitate intermediate steps such as surface blocking and buffer washes. In the sensor instrument, the first and second channels would typically be connected to tubing for the transfer of fluids (usually liquids) to and from the sensor element, the pumping of the fluid being under the control of a user-interfaced module of the instrument. The sensor element carrier may optionally bear an external gasket containing one or more holes in communication with the channels for the ingress or egress of sample fluid, the gasket being connected in use to tubing for the transfer of fluids between the sensor element and the instrument. The interposition of a gasket between the tubing and the sensor element better ensures leak-free communication between instrument and sensor element. The gasket may be integrated into the base or lid component bearing the ingress and egress channels or may be a separate component thereto.

In certain embodiments, the recessed area, and hence the flow cell formed thereby, has a substantially circular shape (i.e. when viewed perpendicularly to the plane of a sensor installed in the sensor element carrier in use). However, other shapes of flow cell are possible in the sensor element carrier of the present invention. For example, rectangular-shaped, elliptical or 'capsule'-shaped (i.e. a circle cut in half and then with the two half-circumferential arcs joined together by two parallel lines). Of these, elliptical and capsule-shaped flow cells may be preferred since they lead to more uniform flow patterns between the channels of fluid ingress and egress compared to a circular flow cell, and, owing to the absence of corners, lead to fewer problems of dead space and accumulation than a rectangular-shaped flow cell.

Preferably, the sensor element carrier also comprises at least two carrier electrodes for connection to the driving and counter electrodes, respectively, of a quartz crystal microbalance received by the base component in use.

The presence of the carrier electrodes within the carrier allows the assembled sensor element to be used for QCM-based sensing simply by connecting a voltage source to the carrier electrodes. Advantageously, the carrier electrodes may be substantially recessed into the base or lid component so as to minimise the interference of the carrier electrodes with the attachment together of the base and lid components. The two carrier electrodes may both be present on the base component or may both be present on the lid component. Preferably, the two carrier electrodes are both present on the base component. The carrier electrodes in such an embodiment may be positioned so as to lie beneath and in contact with a QCM sensor placed into the carrier in use. Alternatively, the carrier electrodes may be resilient or 'rocker' electrodes which, in a first or resting position, do not in come into contact with a sensor element placed into the carrier in use and, in a second or engaged position, contact the driving and counter electrodes of the sensor. The second position may be effected by means of force applied to the rocker electrodes by contacting pins from the associated apparatus of the instrument when the sensor element is engaged therewith in use. When the sensor element is removed from the instrument, the applied force is removed and the rocker electrodes return to their first position. As a further alternative, the sensor element carrier may contain no carrier electrodes, being instead provided with a compressible sealing member which is formed of a material which is electrically conductive only in a direction perpendicular to the plane of a sensor placed into the carrier when the sensor element is assembled for use. Such an arrangement is described further below.

The base component or lid component may have a cavity adjacent the non-sensing surface of the sensor, in use, to avoid damping of the piezoelectric resonance of a sensor based on a quartz crystal microbalance. The cavity should be of a length and width, or diameter (if circular), greater than that of the sensing surface, to ensure minimal damping.

It will be understood that, in a typical embodiment, the component having the cavity will not be the component having the recessed area which forms part of the sample chamber. Indeed, the cavity and the recessed area will be substantially in registration on opposite sides of a QCM sensor placed in the carrier.

In an alternative embodiment, there is an aperture formed in the base or lid component, such that, in use, the non-sensing surface of a sensor based on evanescent wave sensing may be optically accessed. The aperture is preferably formed in the base component.

In this alternative embodiment, the sensing surface of the sensor (e.g. an SPR chip, comprising a glass substrate with a noble metal film on the sensing surface) is within the sample chamber and sealed from the aperture. The non-sensing surface may, however, when the assembled sensor element is coupled to suitable optics and instrumentation, be accessed by a suitable beam of light such that sensing based on evanescent waves propagated thereby at the sensing surface may be carried out.

In certain embodiments, the sensor element carrier can be fitted with a sealable optical window, such that, in use, the sensing surface of a sensor may be interrogated via the optical window by optical means. The optical window may, for example, be sited in the lid component of the carrier. The optical window allows sensor elements comprising such a carrier to be employed for combined mass sensing and microscopy. Such a feature is particularly useful for studies of cells and other particulate systems which typically have a high degree of complexity. Such complexity means that interpretation of mass response data or microscopy data alone is sometimes inadequate. The combination of QCM and microscopy data provides necessary verification of, for instance, cell density and integrity on a sensor surface by microscopy. When the same sensor element is exposed to an analyte that binds to receptors on the cell surface, the binding event can be monitored by the QCM data.

The sealable optical window may be a fixed feature of the sensor element carrier, or may be removable. It will be appreciated that, on re-fitting of the optical window in the latter embodiment, the region of the sensor element carrier containing the optical window is re-sealed thereby. A removable sealable optical window has the advantage of allowing greater access to a sensor mounted in the carrier, e.g. for analyses involving cell preparations.

The optical window may be refractive or non-refractive. A refractive lens can be used to focus the microscopy study to a particular part of the sensor surface that is considered particularly interesting. Such a region may be the centre of the sensor surface since the mass sensitivity of the QCM is highest in this region.

The optical window can be made from any material with a high light transmittance, such as glass, cyclo-olefin polymers (e.g. Zeonor®, available from Zeon Chemical LP), allyl diglycol carbonate (CR-39, available from PPG Industries, Inc), urethane-based pre-polymer (e.g. Trivex®, available from PPG Industries, Inc), AO Alphalite®, Sola Spectralite® (available from Carl Zeiss Vision), Hoya Eyas® (available from Hoya Corporation), polyurethanes, Stylis® (available from Essilor), Hoya Tesalid® (available from Hoya Corporation), or polycarbonates.

In further embodiments, the lid component of the sensor element carrier comprises first and second parts, the first part being adapted for assembly with the base component and having an aperture which, in use, is in registration with a sensor mounted in the carrier, and the second part comprising a plate having a protruding portion shaped such that, on assembly of the sensor element, the protruding portion passes through the aperture to form the recessed area which, in use, and in conjunction with the sensing surface of the sensor, forms the sample chamber.

It will be appreciated that the said first and second parts of the lid component must include substantially rigid portions which come into abutment during assembly of the first and second parts. This ensures the control of sample chamber height achieved by the sensor element carrier of the invention.

In typical embodiments, the lid component comprises first and second parts as described above, the sensor being mounted, in use, in the base component. In preferred embodiments, the first and second parts of the base or lid component are formed entirely from substantially rigid materials. In certain embodiments of the carrier of the invention, the base and/or lid components are formed entirely from a substantially rigid material, such as a rigid plastics material, as described above.

In embodiments of the carrier in which the lid component comprises said first and second parts, the first part may hold the compressible sealing member (e.g. X-ring) and, by its assembly with the base component, the sensor (e.g. QCM crystal) is fixed, in use, in position and is contacted by the electrodes. The centre of the sensing surface of the sensor, e.g. crystal, is freely accessible and can be covered with liquid without risk of leakage, the sensor being sealed between the base component and the first part of the lid component. The second part of the lid component is a plate with a portion protruding from the plate, such that, when the second part is placed on the first part, the flow cell height is defined as described above. Owing to the substantially rigid portions of the base component, and those of the first and second parts of the lid component, the protruding portion of the second part of the lid component is limited in its approach to the sensor, thereby providing control over sample chamber height.

The said second part may be attached to the said first part by means of an adhesive tape. The second part may contain the at least one channel for the ingress of sample fluid, and/or flow channels may be defined in the interface between the said first and second parts, and/or may be defined in the said first part. If flow channels are defined in the interface between the said first and second parts, the adhesive tape may facilitate microfluidic design in this interface in terms of, for instance, sample loops or flow channels that may be accessed from the side of the sensor element carrier facing away from the sensing surface of the sensor in use. This arrangement makes combined microscopy and mass sensing under continuous flow more practical.

It will be appreciated that embodiments of the sensor element carrier in which the lid component comprises said first and second parts can also be used to facilitate microscopy studies. In such embodiments, the second part has, as the protruding portion, the optical window described above.

The possibility of having first an open, well type interface which can readily be transformed into a flowcell (with a defined flowcell height) that can be used for accurate kinetic studies is particularly useful for studies of cells and their interactions with various analytes. The open well design provides for a suitable interface for cell cultivation and preparation which is compatible with many standard cell cultivation techniques.

For example, in a first step the open configuration is used to grow cells on a sensor surface. The sensor surface can be studied by microscopy to determine when the sensor element is ready for biosensor analysis. When the sensor surface has been appropriately coated and is deemed ready the first part of the lid component is mounted and the sensor element is inserted in the sensor system for biosensor analysis, possibly combined with microscopy.

In another aspect of the present invention, there is provided a sensor element carrier for use in a mass-sensitive chemical sensor instrument, the sensor element carrier comprising a base component and a lid component, the base component being adapted to receive, in use, a sensor, the signal generated by which depends on the mass of material adsorbed at a sensing surface thereof, the base component or the lid component having formed therein, in a recessed area, at least one channel for the ingress of sample fluid, the recessed area forming, in use and in conjunction with the sensing surface of the sensor, a sample chamber, the sensor being held, in use, between the base component and the lid component, wherein the lid and/or base component of the sensor element carrier comprises first and second parts, the first part being adapted for assembly with the other of the base or lid components and having an aperture which, in use, is in registration with a sensor mounted in the carrier, and the second part comprising a plate having a protruding portion shaped such that, on assembly of the sensor element, the protruding portion passes through the aperture to form the recessed area which, in use, and in conjunction with the sensing surface of the sensor, forms the sample chamber.

Sensor element carriers according to this other aspect of the invention have the advantage that they can be used for the open-well studies, e.g. involving whole cell preparations, described above. It will be understood that any of the features listed above as optional and/or preferred in relation to the carrier of the first aspect of the invention may also be introduced into the carrier of this other aspect, any modification necessary to introduce such features being within the ability of the skilled person.

In preferred embodiments of the sensor element carrier of this aspect, the first part of the lid component or first part of the base component, or the corresponding base or lid component for assembly therewith, is adapted such that, when the base or lid component and the first part of the lid component or first part of the base component, respectively, are assembled in use with a sensor mounted in the base component, the sensor is sealed between the base component and the first part of the lid component, or between the lid component and first part of the base component, respectively, so as to prevent fluid placed onto the sensor via the aperture in the first part of the lid component or first part of the base component from escaping, other than by means of the said aperture.

Such sealing may be achieved, for example, by means of a gasket interposed between the base or lid component and the first part of the lid component or first part of the base component, respectively. The gasket must, it will be understood, have an aperture in registration with the aperture in the first part of the lid component or first part of the base component, as appropriate. The gasket may, of course, be in the form of the compressible sealing members described above with reference to the first aspect of the invention.

In preferred embodiments of this aspect, the lid component is formed of said first and second parts.

In accordance with a related aspect of the invention, there is provided a sensor element for use in a mass-sensitive chemical sensor instrument, the sensor element comprising a mass-sensitive sensor and a carrier as described above.

In a preferred embodiment, the sensor is a quartz crystal microbalance.

In an alternative embodiment, the sensor is an evanescent wave-based device and the base or lid component of the sensor element carrier has an aperture formed therein for optical access to the non-sensing surface of the sensor.

Preferably, when assembled, and when the sensor is a QCM, the QCM is sealed from the external environment, except for the channels for the ingress and egress of sample fluid. When the sensor is an evanescent wave-based sensor, the sensor is preferably sealed from the external environment, except for the channels for the ingress and egress of sample fluid and the aperture for optical access to the sensor.

The ability to seal the sensor from the external environment reduces the risk of contamination from environmental sources. It also makes it possible to store the sensor element in a 'wet' state, i.e. with the sample chamber containing sample fluid or buffer etc. The sealed nature of the sensor element also makes it more robust than prior art sensor elements.

When the sensor is a QCM, the sensor element preferably comprises a carrier which comprises two electrodes for connection to the driving and counter electrodes of the quartz crystal microbalance, the carrier electrodes being accessible from the exterior of the carrier. The carrier electrodes are preferably accessible via apertures in the base component and/or lid component.

Such an arrangement enhances the isolation which the carrier provides to the sensor. It also enables the sensor element to be readily docked with the associated apparatus of the sensor instrument, simply by placing the sensor element in relation thereto such that suitable electrical contacts from the associated apparatus of the instrument come into contact with the carrier electrodes, e.g. by passing through the apertures in the base and/or lid component.

In embodiments in which the sensor rests on the carrier electrodes, the carrier electrodes should be of low and accurately determinable thickness (e.g. less than 1 mm, preferably less than 0.5 mm). The carrier electrodes also need to be of high conductivity and are therefore preferably gold-plated.

In an alternative embodiment, the sensor element contains no carrier electrodes, and the driving and counter electrodes of the QCM sensor are connected directly to suitable electrical contacts from the associated apparatus of the instrument via holes in the carrier. Such electrical contacts may comprise, for example, retractable pins.

The sensor element may, as a further alternative, be provided with carrier electrodes in the form of 'rocker' electrodes, as described above. In yet a further alternative embodiment, the sensor element contains no carrier electrodes, but the compressible sealing member is formed of a material which is electrically conductive only in a direction perpendicular to the plane of the sensor when the sensor element is assembled. The conductive compressible sealing member may then be electrically contacted to the associated apparatus of the instrument by means of contacting pins provided on the latter and which extend through apertures in the sensor element carrier to allow access to the sealing member.

In embodiments provided with carrier electrodes in the form of 'rocker' electrodes, electrically conductive compressible sealing members, or no carrier electrodes, it will be understood that the considerations discussed above regarding the thickness of the carrier electrodes need not necessarily apply.

In the QCM-based sensor element, the quartz crystal microbalance may comprise a quartz crystal plate provided with a driving electrode on one face of the crystal and a counter electrode on the other face of the crystal, the exposed surface area of each of the driving and counter electrodes being smaller than that of the crystal face on which it is provided such that a peripheral region of the crystal is not provided with electrode material, each of the driving and counter electrodes having a connecting portion which extends towards the periphery of the crystal.

Such a design allows the driving and counter electrodes to be electrically contacted without the carrier electrodes needing to encroach upon the area of the sensing surface which comes into contact with the sample fluid.

Preferably in such an embodiment, the connecting portion of the driving or counter electrode extends to the periphery of the crystal and round to the other face thereof, without contacting the counter or driving electrode, respectively, provided on the other face, such that both the driving and counter electrodes may be contacted from one face of the crystal.

This allows both the carrier electrodes to be present in the base component or both to be present in the lid component of the carrier. It also simplifies engagement of the sensor element with the electrical contacts of the instrument, since those contacts may both readily be engaged with the sensor element from the same side thereof. This is particularly preferred in embodiments containing no carrier electrodes; in this case, the electrical contacts from the associated apparatus of the instrument extend through holes in the carrier and contact the driving and counter electrodes directly from the same face (i.e. that having the non-sensing surface) of the crystal.

In certain preferred embodiments, both driving and counter electrodes can be contacted by carrier electrodes located in the base component. Under such circumstances, the carrier electrodes may preferably be accessible via apertures present in the lid component. In embodiments containing no carrier electrodes, the driving and counter electrodes are preferably accessible via holes present in the base component.

In preferred embodiments of the sensor element of the present invention, the sensing surface of the sensor is at least partially covered with a polymeric coating or a self-assembled monolayer. Such coverage allows increased control and flexibility over the molecular interactions which may be studies using the sensor element.

In certain embodiments of the sensor element carrier and the sensor element of the present invention, the lid component and base component are formed from a material selected from polyoxymethylene, polymethylmethacrylate, polyvinyl chloride and injection-moldable thermoplastics, such as polystyrene or acrylonitrile-butadiene-styrene. However, other known materials would be apparent to the skilled person (taking the present disclosure into account), having regard to the requirements of the carrier described herein.

According to a further aspect of the present invention, there is provided a mass-sensitive chemical sensor instrument comprising a sensor element as described above.

In a related aspect, the present invention also provides the use of a sensor element carrier as described above for constructing a sensor element as described above.

The present invention also provides, in yet another aspect, a method of mass-sensitive chemical sensing, the method comprising introducing a sample fluid through the ingress channel of a sensor element as described above, allowing chemical species within the sample fluid to interact with the sensor and sensing, by means of a change in signal generated by the sensor, such interaction.

In general, the sensor element carrier and sensor element of the present invention achieve significant advantages over prior art sensor elements. The present invention provides accurate and reproducible control over sample chamber height. This is important since it improves kinetic analyses performed using the sensor element (such analyses often being influence by diffusion rate factors which are heavily influenced by sample chamber height). The control over height consistency and reproducibility also allows the attenuation of problems associated with uneven flow speeds of sample fluids. Uneven flow speeds, resulting from differences in sample chamber height, lead to inconsistencies in measurement between samples run using different sensor elements. The ability to build control of sample chamber height into the carrier components also allows a greater flexibility in the range of sample chamber heights which can be prepared. In addition, the ability to seal the sensor element such that the sensor is protected from contamination, even when the sensor element is removed from the instrument, makes the sensor element more useful in a variety of environmental conditions. The sensor element also allows a simple docking to a sensor instrument. The skilled person, having reference to the present disclosure, would immediately appreciate how to adapt existing instrumentation to receive the sensor element of the invention. The instrument would merely need to have a sample insertion unit with appropriate fluidics for introducing fluid samples through the channel(s) in the recessed area of the lid or base component; equipment for measuring the appropriate mass-sensitive characteristics of the sensor (e.g. the piezoelectric properties of a QCM); means for presenting an appropriate signal to the sensor (e.g. electrical contacts for the driving and counter electrodes of a QCM); and associated reservoirs for buffers, waste etc.

The fact that adhesives can be avoided, if necessary, brings advantages in terms of reduction of contamination from the adhesive, either from its leaching into the sample or from its contamination of the sensor surface. When employed, the simplicity of the compressible sealing member of the carrier of the present invention means that it can be fabricated from a variety of high performance resilient materials. This allows the balance between its sealing properties and its low interference with the signal generating properties of the sensor to be optimised. In addition, assembly of the sensor element is considerably more simple and reproducible using a compressible sealing member, such as an 'X'-ring, rather than adhesives. The compressible sealing member is simple to locate within the base or lid component, especially when it can be seated within a groove between the recessed and non-recessed areas thereof. Furthermore, assembly is quicker since there is no need to laboriously place a continuous bead of adhesive on the carrier before the sensor can be placed.

The invention will now be described in more detail by way of example only and with reference to the appended drawings, of which:

Figure 1:
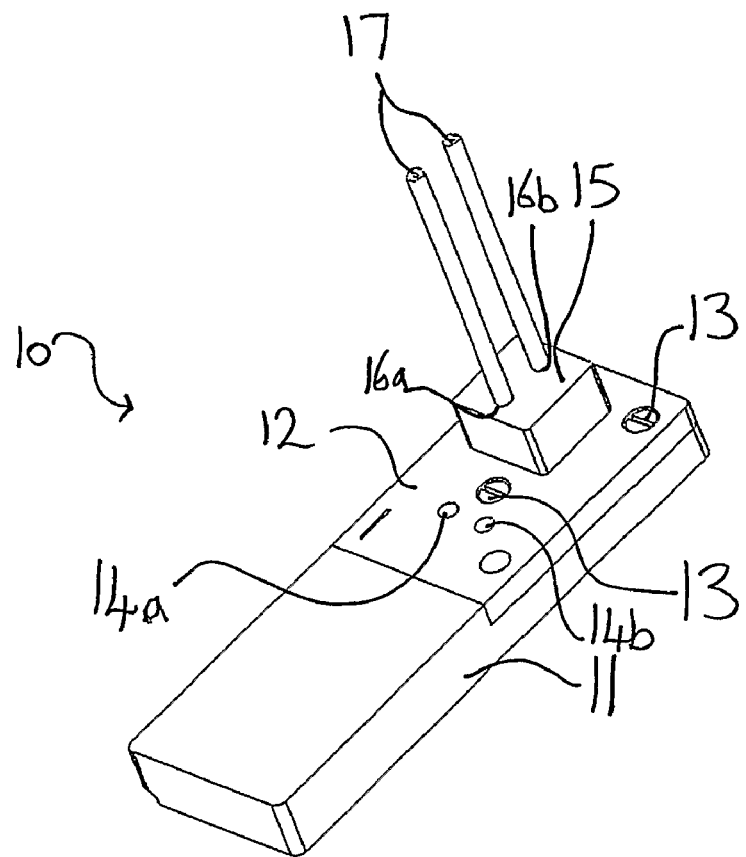
FIG. 1 shows a perspective view of a sensor element according to the present invention, assembled and bearing a rubber gasket connected to tubing.

Turning first to FIG. 1, the sensor element, generally indicated 10 comprises a base component 11 and a lid component 12 connected thereto by means of screws 13. Both lid and base components are formed from the substantially rigid plastics material polyoxymethylene. The lid component 12 has two apertures 14a, 14b for the connection of electrical contacts (e.g. plugs connected to wires) from a sensor instrument, such as an Attana A100 QCM instrument. The lid component 12 has connected thereto a rubber gasket 15 having two holes 16a, 16b therethrough. Tubing 17 is connected to holes 16a,b for the transfer of sample fluids, buffers etc. between the sensor element and the instrument.

Figure 2:
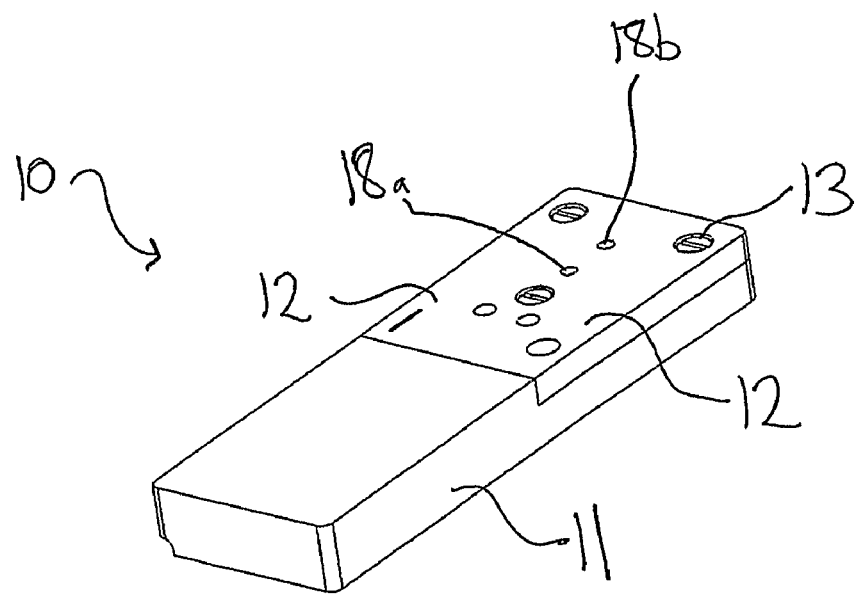
FIG. 2 shows the sensor element of FIG. 1 with the gasket and tubing removed.

On removal of the gasket 15 (FIG. 2 and FIG. 4), the lid component can be seen to contain two holes 18a,18b. As will be described in more detail below, holes 18a,b are channels through which sample fluids etc. can be introduced to a sensor residing within the sensor element.

Figure 3:
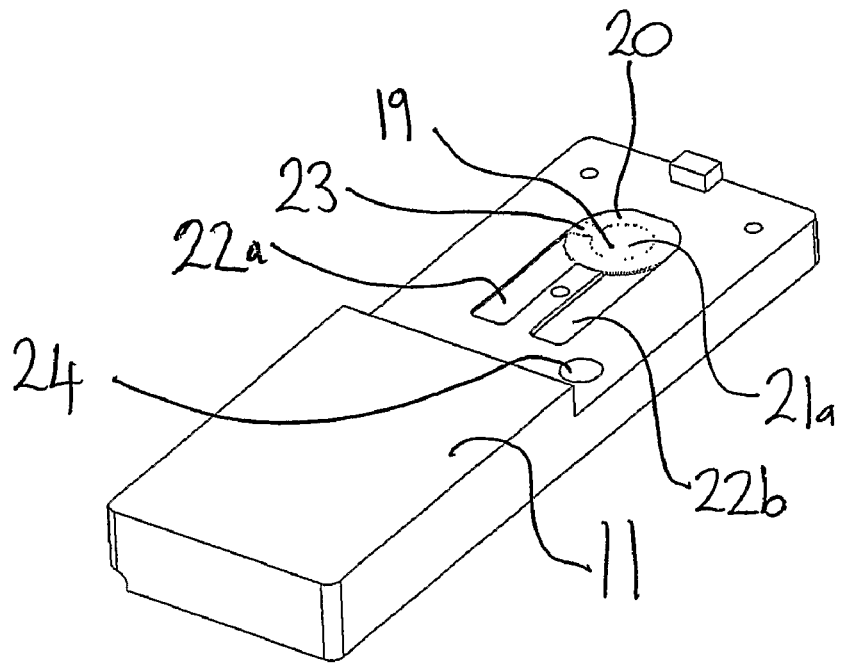
FIG. 3 shows the sensor element of FIGS. 1 and 2 with the lid component removed.

Internally of the sensor element (FIG. 3), and in the base component 11 thereof, are positioned a QCM sensor 19 comprising a quartz crystal 20 and gold driving and counter electrodes 21a, 21b (only one of these electrodes is visible in FIG.

3) on either face thereof. The base component also contains two carrier electrodes 22a, 22b for connection to the driving and counter electrodes 21a,b. The carrier electrodes 22a,b connect to portions 23 of the electrodes 21a,b which extend away from the main portions of the latter towards the periphery of the crystal 20. In the case of electrode 21a, the extending portion 23 continues around the side of the crystal 20 to terminate in a connecting portion on the underside of the crystal 20 which is, however, separated from electrode 21b by bare quartz crystal. In this way, carrier electrode 22a may be electrically connected to electrode 21a and carrier electrode 22b may be electrically connected to electrode 21b despite the fact that both carrier electrodes 22a,b are situated adjacent the same face of the QCM sensor 19. The carrier electrodes 22a,b are, when the sensor element is assembled, in registration with apertures 14a,b of the lid component, for the connection of electrical contacts for the generation of an AC voltage which causes the QCM 19 to resonate.

The base component 11 also has a hole or depression 24, and the lid component 12 has a hole 25 in registration with the hole or depression 24. When the sensor element 10 is assembled, holes 24 and 25 facilitate the correct positional docking of the sensor element in the QCM sensor instrument by means of a peg provided on the latter and designed to pass through hole 25 and into hole 24.

Figure 4:
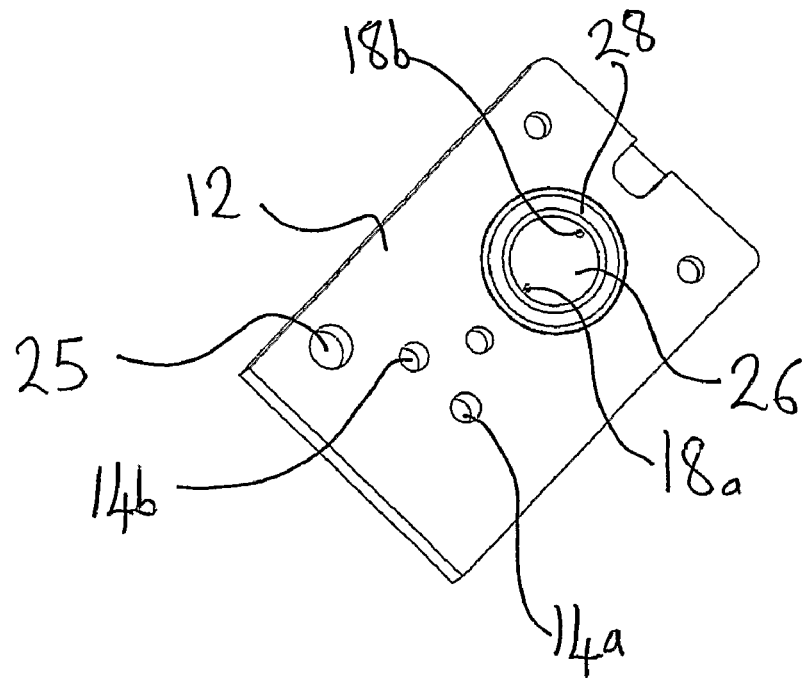
FIG. 4 shows a perspective view of the underside of the lid component of the sensor element of FIGS. 1 to 3, complete with an X-ring.
Figure 5:
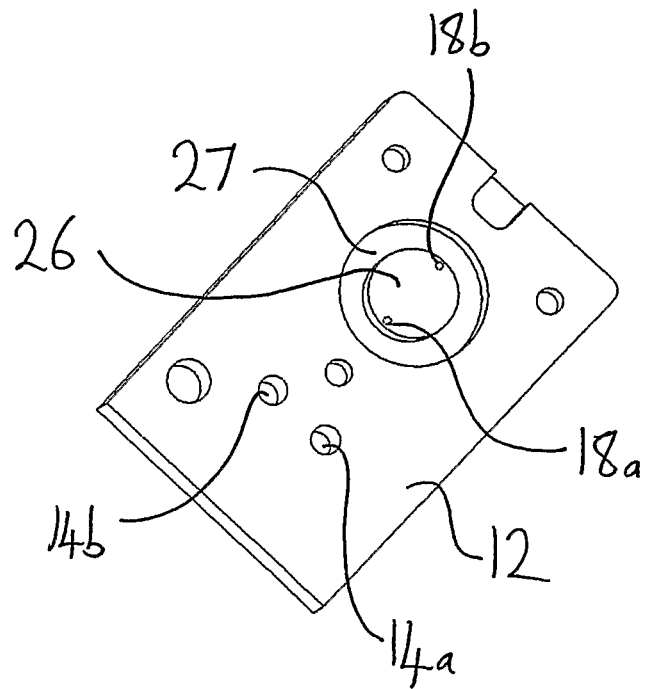
FIG. 5 shows the lid component of FIG. 4 with its X-ring removed.

The underside of the lid component 12 has a recessed area 26 surrounded by a deeper groove 27 (FIGS. 4 and 5). In the recessed area 26 can be seen the other ends of the holes or channels 18a,b, through which sample fluids etc. are introduced to the QCM sensor. The groove 27 is fitted with a resilient and compressible ring 28 (see FIG. 4) having a substantially 'X'-shaped cross section (the X-ring).

Figure 6:
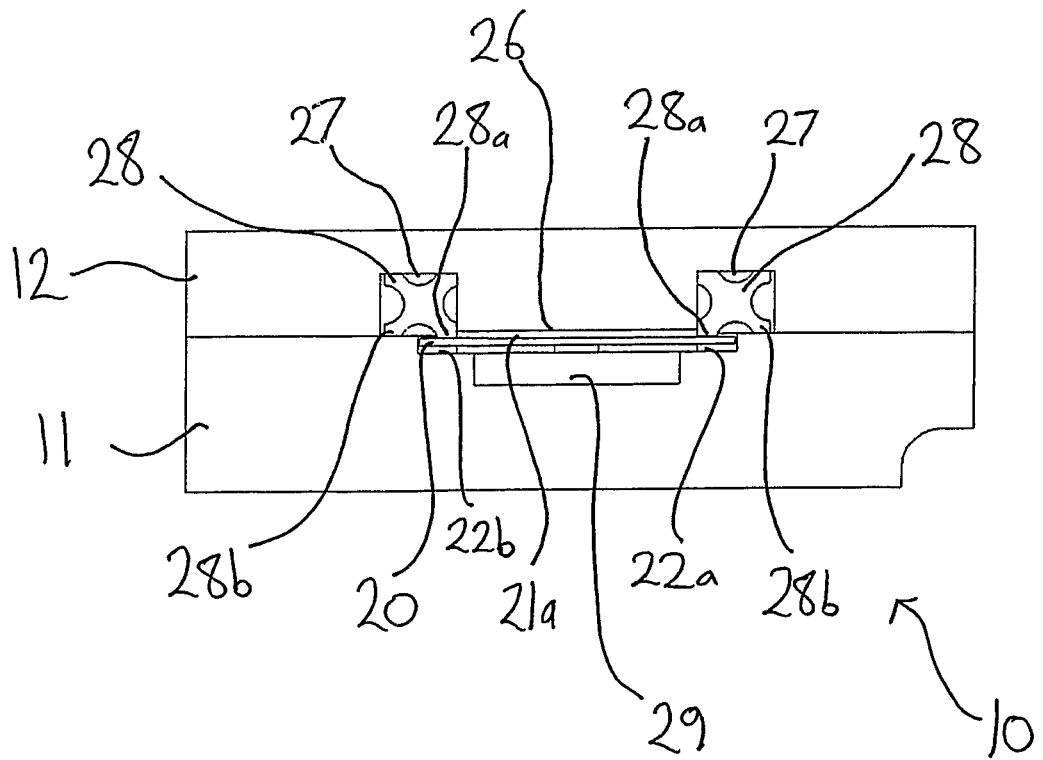
FIG. 6 shows a schematic cross section, in the region of the sensor, through the sensor element of FIGS. 1 and 2.
Figure 7:
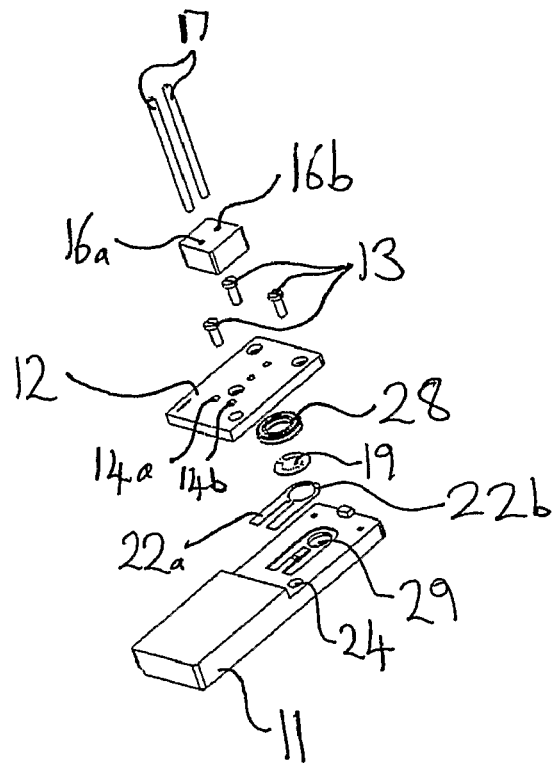
FIG. 7 shows an exploded perspective view of the assembled sensor element of FIGS. 1 and 2.

When the sensor element is assembled, the X ring 28 is compressed against the outer edges of the QCM crystal 20 (see FIG. 6). Only the inner legs 28a of the cross section of the X-ring are compressed against the crystal 20, whilst the outer legs 28b are compressed against the upper surface of the base component 11. Due to the level of the upper surface of the crystal 20 being lower than the upper surface of the surrounding region of the base component, the compression of the legs 28b is greater than that of legs 28a. The pressure exerted against the crystal 20 due to only a small area of the X-ring 28 being compressed thereagainst results in an effective seal without excessive damping of the piezoelectric resonance of the crystal or other damage thereto. Since the outer legs 28b have a higher sealing compression, this reduces the risk of liquids encroaching into the sensor element from outside. As can be clearly seen in FIG. 6, the ceiling of the sample chamber, formed by the recessed area 26 of the lid component 12, cannot approach the upper surface of the QCM sensor any more closely since the portions of the lid and base components externally of the X-ring 28 abut each other. The sample chamber height is thus predictable, reproducible and controllable. Further tightening of screws 13 therefore does not alter the sample chamber height. Furthermore, as a result of the abutment of the lid and base components during assembly, over-tightening of the screws 13 is discouraged since the user will clearly be able to sense once the screws have been sufficiently tightened. This helps prevent mechanical damage to the sensor element, particularly the carrier. In preferred embodiments, the screws 13 have flat leading ends. Since the base component is preferably formed with screw-receiving receiving holes which are blind-ended, it is very clear to the user, when assembling the sensor element, when the screws have been inserted sufficiently, both as a result of the abutment of the lid and base components and as a result of the ends of the screws 13 being unable to travel further through the holes in the base component.

Beneath the QCM sensor 19 is a cavity 29 formed in the base component 11 and which allows the QCM crystal to resonate.

Figure 8:
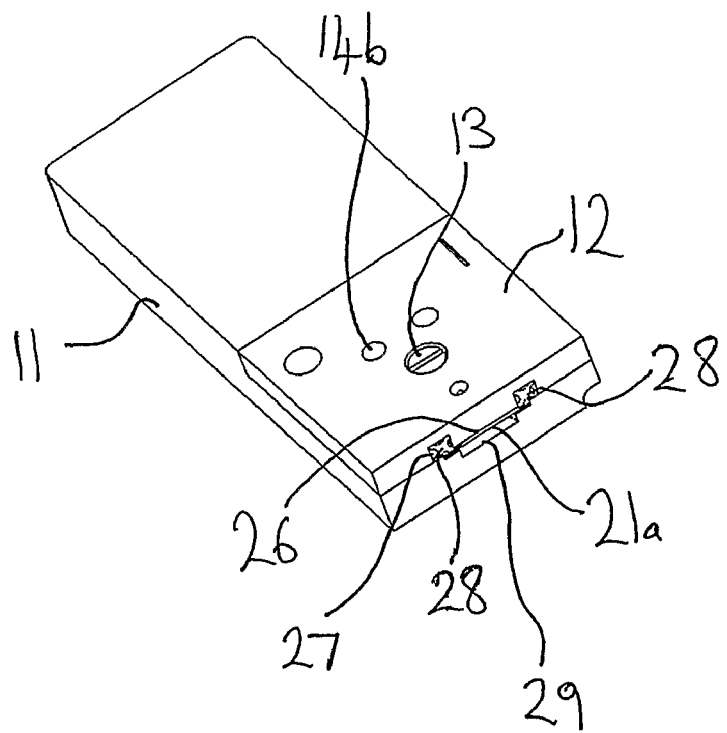
FIG. 8 shows a perspective view of the sensor element of FIGS. 1 and 2, cut transversely in the region of the sensor.

In another embodiment, the X-ring 28 and the groove 27 can be omitted. In such an embodiment, a layer of adhesive can be applied to the outer edges of the upper surface of the crystal 20. The adhesive allows the crystal to be sealingly adhered to the underside of the lid component in the region immediately surrounding the recessed area 26. On assembly of the sensor element, the layer of adhesive becomes compressed between the lid component and crystal, under pressure from the base component. The result of this arrangement is that, once the base and lid components abut (i.e. as shown in FIGS. 6 and 8), the layer of adhesive is compressed to an appropriate degree such that, as in the embodiment using the X-ring, the sample chamber height is predictable and reproducible, regardless of the thickness of the adhesive layer which would typically be applied in securing the sensor to the sensor element carrier.

Figure 9:
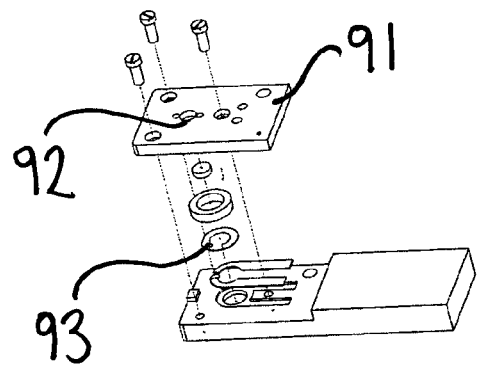
FIG. 9 shows an exploded perspective view of a sensor element of the invention including an optical window for facilitating optical interrogation of the sensor surface.

In FIG. 9, the lid component 91 is provided with a sealable optical window 92 which allows optical interrogation of the sensing surface of the QCM crystal 93. In all other aspects, the sensor element of FIG. 9 is essentially identical to the sensor element described above with reference to FIGS. 1-8.

The sensor element shown in FIG. 9 was used to conduct a combined QCM/microscopy study. The study was conducted as follows:

Step 1

Figure 10:
FIG. 10 shows a fluorescence micrograph of the sensing surface of a QCM crystal mounted in a sensor element carrier of the present invention and having an optical window.

RAW cells (a mouse leukaemic monocyte macrophage cell line) were introduced onto the sensing surface of the QCM crystal. The sensor element was mounted into a standard fluorescence microscope. A control photomicrograph was taken through the optical window (92—FIG. 9) of the sensor element before the injection of fluorescently-tagged lectin. The cells on the surface prior to lectin injection gave a weak auto-fluorescence response (FIG. 10).

Step 2

Figure 11:
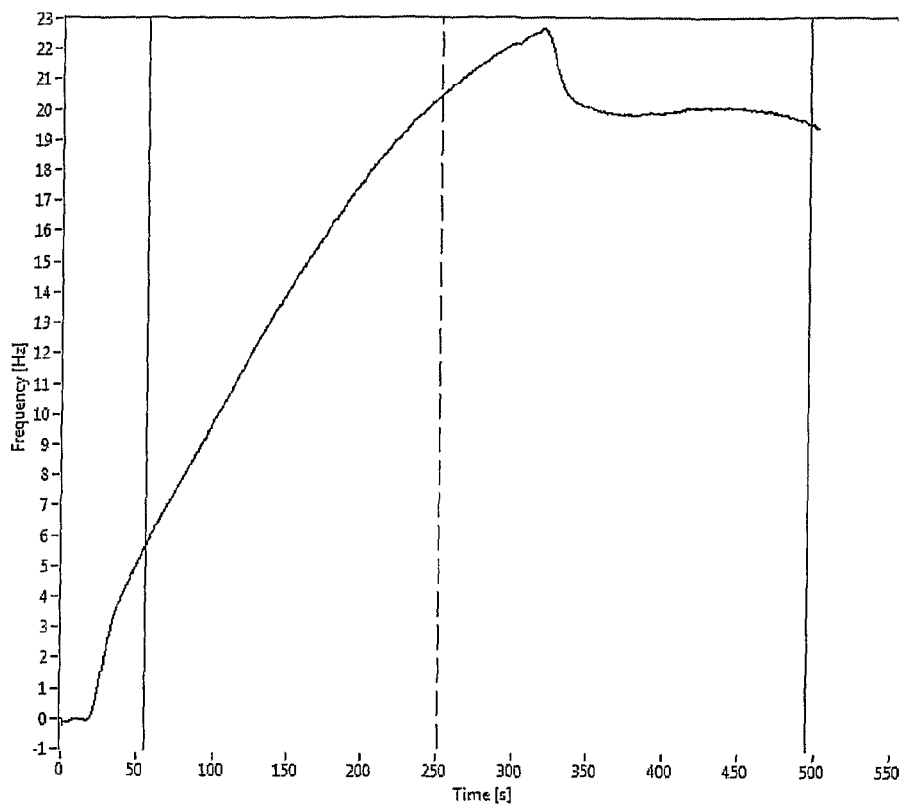
FIG. 11 shows a QCM trace for the crystal of FIG. 10 following mounting of the sensor element in a QCM instrument and the injection of a fluorescently-tagged lectin into the element.

The sensor element is mounted into an Attana A100 instrument. The resonance frequency of the QCM sensor shifts approximately 22 Hz during the lectin injection indicating that the lectin is immobilised on the cell surface (see FIG. 11).

Step 3

Figure 12:
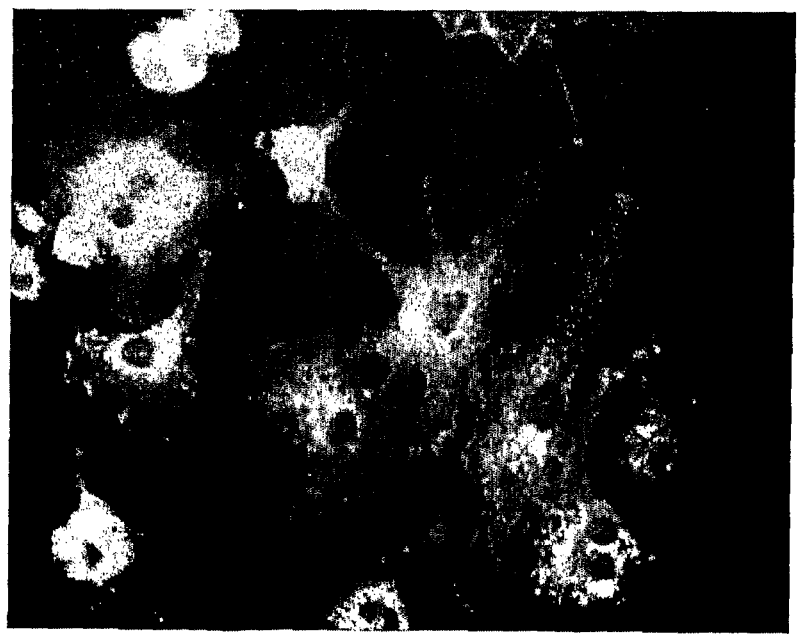
FIG. 12 shows a fluorescence micrograph of the sensing surface of the QCM crystal of FIG. 10, following the lectin binding experiment of FIG. 11.

The sensor element is again mounted into a standard fluorescence microscope. A photomicrograph taken through the optical window after the experiment reveals a distinct fluorescence signal—confirming that the lectin has bound to the surface of the cells on the sensor (FIG. 12).

Figure 13:
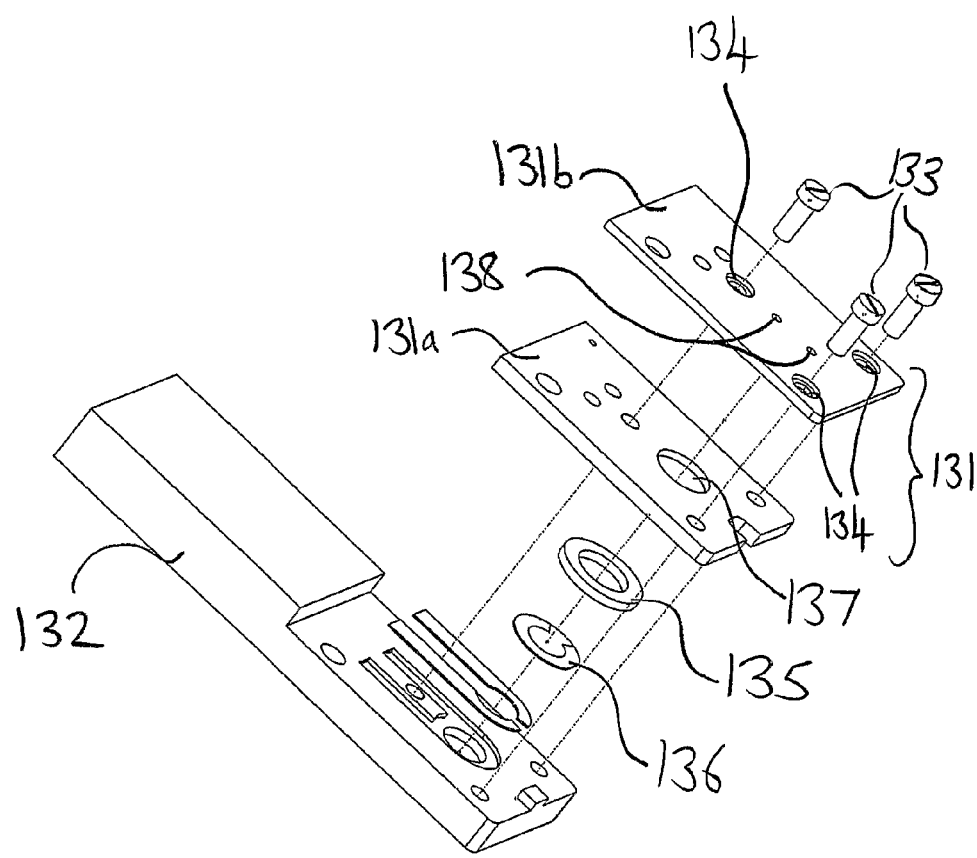
FIG. 13 shows an exploded perspective view, from above, of a sensor element of the invention having a lid component comprising first and second parts.

In FIG. 13, the sensor element comprises a carrier in which the lid component 131 is formed of two parts 131a and 131b. The other components of the sensor element are essentially the same as described above with reference to FIGS. 1-8. The first part 131a fixes to the base component 132 by means of screws 133 which pass through holes 134 in the second part 131b. The screws do not, however, fix the first and second parts 131a,b to each other; they merely pass through holes 134 to fix the first part 131a to the base component 132. A compressible sealing member, as described above and indicated 135, is positioned between the first part 131a and the QCM sensor 136. As can be more clearly seen in FIG. 14, when the second part 131b is fixed to the first part 131a, for example by means of an adhesive tape (not shown), a protruding cylindrical-shaped portion 141 of the second part 131b passes through an aperture 137 in the first part 131a, the protruding face of portion 141 thereby forming the sample chamber in conjunction with the sensing surface of the sensor and the inner walls of the compressible sealing member 135. It will be noted that the channels (indicated 138) for the ingress and egress of sample fluid are located within the protruding portion 141.

Figure 15:
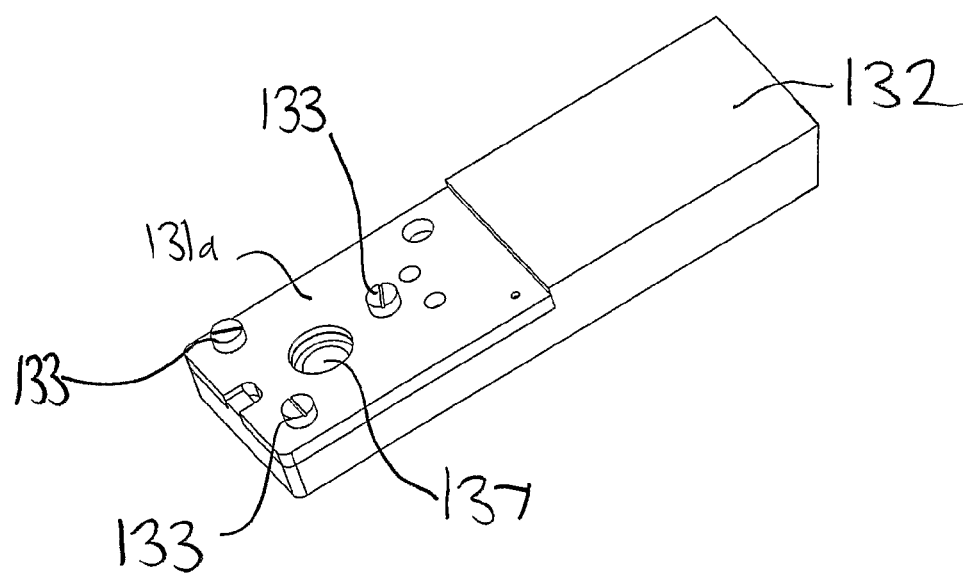
FIG. 15 shows the sensor element of FIGS. 10 and 11, partially assembled with the first part of the lid component in place.

When the second part 131*b* is removed, the aperture 137 allows ready access to the sensing surface of the sensor (FIG. 15). This allows the introduction of analytical materials, e.g. cells or particulates, which are less amenable to introduction via the channels 138. It also allows the sensor element to be used for culturing of cells prior to analysis. The sensor is sealed between the base component 132 and the first part 131*a*, such that liquids etc. introduced into the 'open' element (as shown in FIG. 15) will not leak away from the sensor during storage or incubation steps.

Figure 14:
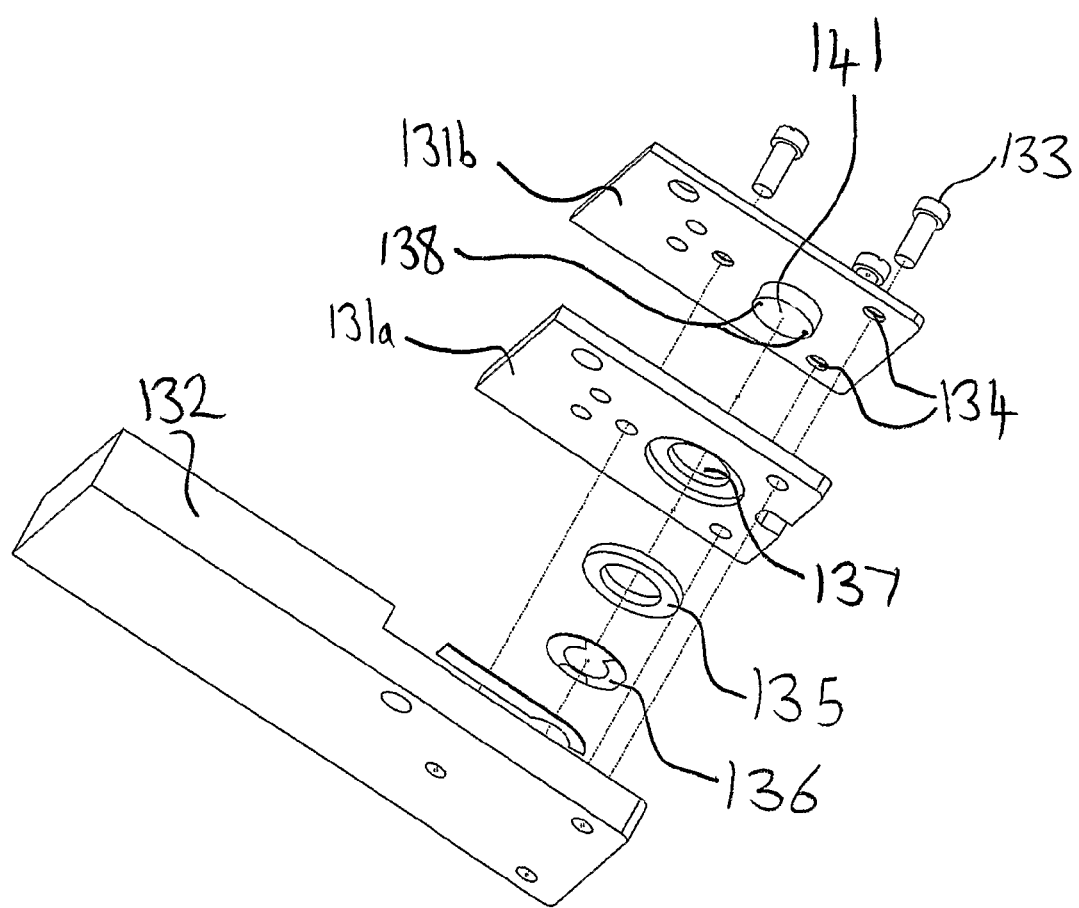
FIG. 14 shows the sensor element of FIG. 10, in exploded perspective view, from below.

The sensor element shown in FIG. 13-15 may also be used for microscopy studies. Microscopic interrogation of the sensor surface may be conducted either using the 'open' element approach shown in FIG. 15, or may be achieved by incorporating an optical window (as in FIG. 9) into the protruding portion 141. The latter arrangement has the advantage that the sensor element does not have to be repeatedly opened for microscopic analysis during QCM experiments, thereby further opening up the possibility of combining biosensing and microscopy in the same instrument.

The foregoing Examples are intended to illustrate specific embodiments of the present invention and are not intended to limit the scope thereof, the scope being defined by the appended claims. All documents cited herein are incorporated herein by reference in their entirety.

The invention claimed is:

1. A sensor element carrier for use in a mass-sensitive chemical sensor instrument, comprising:
   (a) a base component;
   (b) a lid component;
   (c) a sample chamber formed from a recess area of the base component or the lid component and, when in use, comprising a sensor having a sensing surface, a signal generated by which depends on the mass of material adsorbed at the sensing surface thereof; and
   (d) at least one channel—for the ingress of a sample fluid, in the—recessed area, and wherein the base component and the lid component having substantially rigid portions are limited on assembly of the sensor element when in use, by the substantially rigid portions of each which come into abutment, thereby limiting the minimum height of the sample chamber for a given set of sensor, base and lid components.

2. The sensor element carrier according to claim 1, further comprising a compressible sealing member surrounding the recessed area, wherein the compressible sealing member protrudes beyond the recessed area and beyond the non-recessed portion of the base or lid component surrounding the recessed area, such that the compressible sealing member abuts, in use, the surface of the sensor so as to form a plurality of lateral edges of the sample chamber.

3. The sensor element carrier according to claim 2 wherein the compressible sealing member is an elastomeric ring having a cross-sectional shape which is capable of deformation, upon application of axial force, by bending.

4. The sensor element carrier according to claim 3 wherein the compressible sealing member is an elastomeric ring having an 'X'-shaped, or equivalent, cross section.

5. The sensor element carrier according to claim 4 wherein, in use, the elastomeric ring and the sensor are arranged such that only the inner protruding leg of the 'X'-shaped, or equivalent, cross section contacts the sensor and is less compressed than an outer protruding leg, wherein the outer protruding leg contacts the base component or lid component.

6. The sensor element carrier according to claim 1, wherein the recessed area having the at least one channel is formed in the lid component.

7. The sensor element carrier according to claim 1, wherein the recessed area has a first channel formed therein for the ingress of sample fluid, and a second channel formed therein for the egress of sample fluid, such that the sample chamber can be used as a flow cell.

8. The sensor element carrier according to claim 1, further comprising at least two carrier electrodes for connecting to a driving and counter electrodes.

9. The sensor element carrier according to claim 1, wherein the base component or lid component has a cavity adjacent the non-sensing surface of the sensor, when in use, to avoid damping of the piezoelectric resonance of a sensor based on a quartz crystal microbalance.

10. The sensor element carrier according to claim 1, wherein an aperture is formed in the base component or lid component, such that, when in use, the non-sensing surface of a sensor based on evanescent wave sensing is optically accessed.

11. The sensor element carrier according to claim 1, wherein the sensor element carrier is fitted with a sealable optical window, such that, when in use, the sensing surface of a sensor is interrogated via the optical window.

12. The sensor element carrier according to claim 1, wherein the lid component of the sensor element carrier comprises a first part and a second part, wherein the first part is being adapted for assembly with the base component and has an aperture which, when in use, is in registration with a sensor mounted in the carrier, and wherein the second part comprises a plate having a protruding portion shaped such that, on assembly of the sensor element, the protruding portion passes through the aperture to form the recessed area which, when in use, and in conjunction with the sensing surface of the sensor, forms the sample chamber.

13. The carrier according to claim 1 wherein the lid component and base component are formed from a material selected from the group consisting of polyoxymethylene, polymethylmethacrylate, polyvinyl chloride and injection-moldable thermoplastics, polystyrene, acrylonitrile-butadiene-styrene, and composites thereof.

14. The sensor element carrier according to claim 1, wherein the sensing surface of the sensor is at least partially covered with a polymeric coating or a self-assembled monolayer.

15. A sensor element for use in a mass-sensitive chemical sensor instrument, comprising a mass-sensitive sensor having a sensing surface and a carrier wherein the carrier comprises:
   (a) a base component;
   (b) a lid component;
   (c) a sample chamber formed from a recess area of the base component or the lid component; and
   (d) at least one channel—for the ingress of a sample fluid in the recess area, and wherein base component and the lid component have substantially rigid portions are limited on assembly of the sensor element, when in use, by the substantially rigid portions of each which come into abutment, thereby limiting the minimum height of the sample chamber for a given set of sensor, base and lid components.

16. The sensor element according to claim 15, wherein the sensor is a quartz crystal microbalance, wherein, when assembled, the quartz crystal microbalance is sealed from the external environment, except for the channels for the ingress and egress of sample fluid.

17. The sensor element according to claim 15, wherein the sensor is an evanescent wave-based device and the base or lid component of the sensor element carrier has an aperture formed therein for optical access to the non-sensing surface of the sensor.

18. The sensor element according to claim 16 wherein the carrier comprises two electrodes for connection to the driving and counter electrodes of the quartz crystal microbalance, the carrier electrodes being accessible from the exterior of the carrier.

19. The sensor element according to claim 18 wherein the carrier electrodes are accessible via apertures in the base component or lid component.

20. The sensor element according to claim 16, wherein the quartz crystal microbalance comprises a quartz crystal plate having a first face and a second face, and provided with a driving electrode having an exposed surface on the first face of the quartz crystal plate and a counter electrode having an exposed surface on the second face of the quartz crystal plate, wherein the exposed surface area of each of the driving electrode and counter electrodes is smaller than that of the first and second crystal faces on which it is provided, whereby a peripheral region of the crystal is not provided with electrode material, and whereby each of the driving and counter electrodes has a connecting portion extending towards a periphery of the quartz crystal plate.

21. The sensor element according to claim 20 wherein the connecting portion of the driving or counter electrode extends to the periphery of the first face of the quartz crystal plate and round to the second face thereof, without contacting the counter or driving electrode, respectively, provided on the second face of the quartz crystal plate, whereby both the driving and counter electrodes are contacted from one face of the quartz crystal plate.

22. The sensor element according to claim 20 wherein both driving and counter electrodes are contacted by carrier electrodes located in the base component.

23. The sensor element according to claim 15, wherein the sensing surface of the sensor is at least partially covered with a polymeric coating or a self-assembled monolayer.

24. The sensor element according to claim 15, wherein the lid component and base component are formed from a material selected from the group consisting of polyoxymethylene, polymethylmethacrylate, polyvinyl chloride and injection-moldable thermoplastics, polystyrene, acrylonitrile-butadiene-styrene, and composites thereof.

25. A mass-sensitive chemical sensor instrument, comprising a sensor element, wherein the sensor element comprises a mass-sensitive sensor having a sensing surface and a carrier wherein the carrier comprises:
  (a) a base component;
  (b) a lid component;
  (c)) a sample chamber formed from a recess area of the base component or the lid component and comprising, when in use, the sensor element; and
  (d) at least one channel—for the ingress of a sample fluid, and wherein base component and the lid component have substantially rigid portions are limited on assembly of the sensor element, when in use, by the substantially rigid portions of each which come into abutment, thereby limiting the minimum height of the sample chamber for a given set of sensor, base and lid components.

26. A method for mass-sensitive chemical sensing, comprising:
  (1) introducing a sample fluid through an ingress channel of a sensor element, wherein the sensor element comprises a mass-sensitive sensor and a carrier comprising:
    (a) a base component wherein the base component is adapted to receive a lid component in use;
    (b) a lid component;
    (c) a sample chamber formed from a recess area of the base component or the lid component,
    (d) at least one channel for the ingress of a sample fluid, and wherein base component and the lid component have substantially rigid portions are limited on assembly of the sensor element, when in use, by the substantially rigid portions of each which come into abutment, thereby limiting the minimum height of the sample chamber for a given set of sensor, base and lid components;
  (2) allowing chemical species within the sample fluid to interact with the sensor; and
  (3) sensing, by means of a change in signal generated by the sensor, such interaction.

27. A sensor element carrier for use in a mass-sensitive chemical sensor instrument, the sensor element carrier comprising a base component and a lid component, the base component being adapted to receive, in use, a sensor, the signal generated by which depends on the mass of material adsorbed at a sensing surface thereof, the base component or the lid component having formed therein, in a recessed area, at least one channel for the ingress of sample fluid, the recessed area forming, in use and in conjunction with the sensing surface of the sensor, a sample chamber, the sensor being held, in use, between the base component and the lid component, wherein the lid and/or base component of the sensor element carrier comprises first and second parts, the first part being adapted for assembly with the other of the base or lid components and having an aperture which, in use, is in registration with a sensor mounted in the carrier, and the second part comprising a plate having a protruding portion shaped such that, on assembly of the sensor element, the protruding portion passes through the aperture to form the recessed area which, in use, and in conjunction with the sensing surface of the sensor, forms the sample chamber.

28. A sensor element carrier according to claim 27, wherein the first part of the lid component or first part of the base component, or the corresponding base or lid component for assembly therewith, is adapted such that, when the base or lid component and the first part of the lid component or first part of the base component, respectively, are assembled in use with a sensor mounted in the base component, the sensor is sealed between the base component and the first part of the lid component, or between the lid component and first part of the base component, respectively, so as to prevent fluid placed onto the sensor via the aperture in the first part of the lid component or first part of the base component from escaping, other than by means of the said aperture.

* * * * *